US008616238B2

(12) United States Patent
Lee

(10) Patent No.: US 8,616,238 B2
(45) Date of Patent: Dec. 31, 2013

(54) FLOW SELECTOR

(75) Inventor: Freddie Eng Hwee Lee, Singapore (SG)

(73) Assignee: B. Braun Melsungen AG, Melsungen (DE)

( * ) Notice: Subject to any disclaimer, the term of this patent is extended or adjusted under 35 U.S.C. 154(b) by 712 days.

(21) Appl. No.: 12/839,067

(22) Filed: Jul. 19, 2010

(65) Prior Publication Data
US 2012/0012215 A1    Jan. 19, 2012

(51) Int. Cl.
F16K 11/085    (2006.01)

(52) U.S. Cl.
USPC .................................. 137/625.47; 137/556.6

(58) Field of Classification Search
USPC ......... 137/625.46–625.47, 556.3, 556.6, 876, 137/872
See application file for complete search history.

(56) References Cited

U.S. PATENT DOCUMENTS

| 3,134,403 | A | * | 5/1964 | Rudelick ................... 137/625.16 |
| 3,618,637 | A | | 11/1971 | Santomieri |
| 3,998,227 | A | * | 12/1976 | Holbrook et al. .............. 604/119 |
| 4,263,937 | A | * | 4/1981 | Rudenko ........................ 601/136 |
| 4,397,335 | A | * | 8/1983 | Doblar et al. ............. 137/625.19 |
| 4,553,566 | A | * | 11/1985 | Barclay et al. ............ 137/625.11 |
| 4,802,650 | A | | 2/1989 | Stricker |
| 5,105,983 | A | | 4/1992 | Sancoff et al. |
| 5,360,411 | A | | 11/1994 | Mimura et al. |
| 6,135,153 | A | | 10/2000 | Cleland et al. |
| 7,618,432 | B2 | | 11/2009 | Pedersen et al. |
| 7,803,133 | B2 | | 9/2010 | Lee |
| 8,092,417 | B2 | | 1/2012 | Kim |
| 2004/0173167 | A1 | | 9/2004 | Chanfreau et al. |
| 2005/0277883 | A1 | | 12/2005 | Kriesel |
| 2005/0277884 | A1 | | 12/2005 | Kriesel et al. |
| 2006/0229558 | A1 | | 10/2006 | Heston et al. |
| 2007/0006621 | A1 | | 1/2007 | Doong |
| 2008/0017260 | A1 | * | 1/2008 | Oh et al. ..................... 137/625.3 |
| 2008/0177233 | A1 | * | 7/2008 | Lee ............................... 604/151 |

FOREIGN PATENT DOCUMENTS

| DE | 43 23 613 | 1/1995 |
| EP | 0 577 354 | 1/1994 |
| EP | 0 800 837 | 10/1997 |
| EP | 0 885 620 | 12/1998 |
| WO | WO 2008/011264 | 1/2008 |

OTHER PUBLICATIONS

Office Action for U.S. Appl. No. 12/835,209 mailed Feb. 2, 2012.
International Search Report for PCT/IB2011/001660 dated Jan. 27, 2012.
International Search Report for PCT/IB2011/001621 dated Jan. 19, 2012.

* cited by examiner

*Primary Examiner* — John Rivell
*Assistant Examiner* — David Colon Morales
(74) *Attorney, Agent, or Firm* — RatnerPrestia

(57) ABSTRACT

An apparatus for selecting a flow rate of a fluid includes a barrel including an output port and a plurality of input ports; and an axle disposed substantially concentrically within the barrel. A plurality of drain channels are formed in an outer surface of the axle, each drain channel having a depth less than a thickness of a wall of the axle. The axle is rotatable within the barrel to provide one of a plurality of flow paths between one of the plurality of input ports and the output port, each flow path at least partially defined by at least one of the drain channels.

19 Claims, 15 Drawing Sheets

SECTION C-C

FLOW SELECTOR

BACKGROUND

A flow selector regulates the flow rate of a fluid from a source, e.g., a fluid pump, to a final receiving point, e.g., a patient, through one or more fluid-carrying channels, e.g., polyvinyl chloride (PVC) or silicone-based tubes. In the context of a patient receiving medication, a flow selector allows for adjustment of the dose of medication as deemed appropriate during therapy. Flow selectors have been used in conjunction with fluid pumps that have fixed rates of flow output.

SUMMARY

In a general aspect, an apparatus for selecting a flow rate of a fluid includes a barrel including an output port and a plurality of input ports; and an axle disposed substantially concentrically within the barrel. A plurality of drain channels are formed in an outer surface of the axle, each drain channel having a depth less than a thickness of a wall of the axle. The axle is rotatable within the barrel to provide one of a plurality of flow paths between one of the plurality of input ports and the output port, each flow path at least partially defined by at least one of the drain channels.

Embodiments may include one or more of the following.

The axle is formed of a plurality of axle segments, each axle segment having a different radius.

The barrel is formed of a plurality of barrel segments, each barrel segment having a different radius, each barrel segment corresponding to one of the plurality of axle segments. An outer surface of each of the plurality of axle segments is in contact with an inner surface of the corresponding one of the plurality barrel segments. At least one gap is present between the axle and the barrel, each gap located at a boundary between one of the plurality of barrel segments and an adjacent one of the plurality of barrel segments. At least one of the plurality of flow paths is further defined by the at least one gap. A drain cavity is formed in the inner surface of at least one of the plurality of barrel segments, at least one of the plurality of flow paths further defined by the drain cavity. Each barrel segment corresponds to one of the plurality of input ports The plurality of drain channels are formed in an outer surface of the plurality of axle segments. Each flow path is defined by no more than one drain channel on each of the plurality of axle segments.

The flow rate of the fluid is selected by rotating the axle to a position such that at least one of the plurality of drain channels is aligned with at least one of the plurality of input ports. The flow rate of the fluid comprises the sum of the flow rates of the fluid through the at least one of the plurality of input ports aligned with the at least one of the plurality of drain channels.

The apparatus further includes a control knob configured to rotate the axle. The control knob includes a plurality of position identifiers, each position identifier corresponding to one of the plurality of flow paths. The control knob is removable, and wherein rotation of the axle is prohibited after removal of the control knob.

The number of flow paths is $2^N-1$, where N is the number of input ports.

At least some of the plurality of flow paths correspond to different flow rates.

The barrel includes a groove configured to receive a stabilizer ring formed on the outer surface of the axle.

The flow selector described herein has a number of advantages. Without apertures or holes in the axle, the tooling needed to fabricate the flow selector can be significantly simplified. This simplicity reduces manufacturing cost and/or allows a large number of flow rate combinations to be incorporated into a single device. In cases where a specific flow rate cannot be derived from the combinations of flow rates already available from the fixed number of inlet ports in a particular device, additional inlet ports can be added without presenting significant technical difficulties in the fabrication of the new inlet ports. As new drugs are introduced that require new doses, this flexibility frees the user from the restrictions of adjusting doses to fit into fixed flow rate pumps. In addition, the flow selector can be packaged in a compact, user-friendly design.

Other features and advantages of the invention are apparent from the following description and from the claims.

DETAILED DESCRIPTION

Figure 1A:
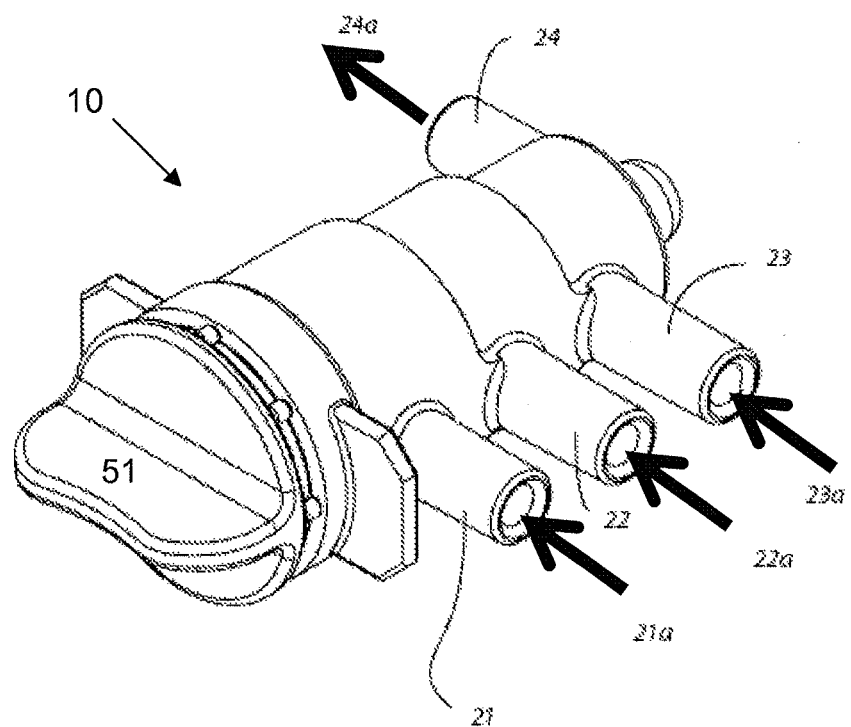
FIGS. 1A and 1B are a perspective view and a side view, respectively, of a flow selector.
Figure 1B:
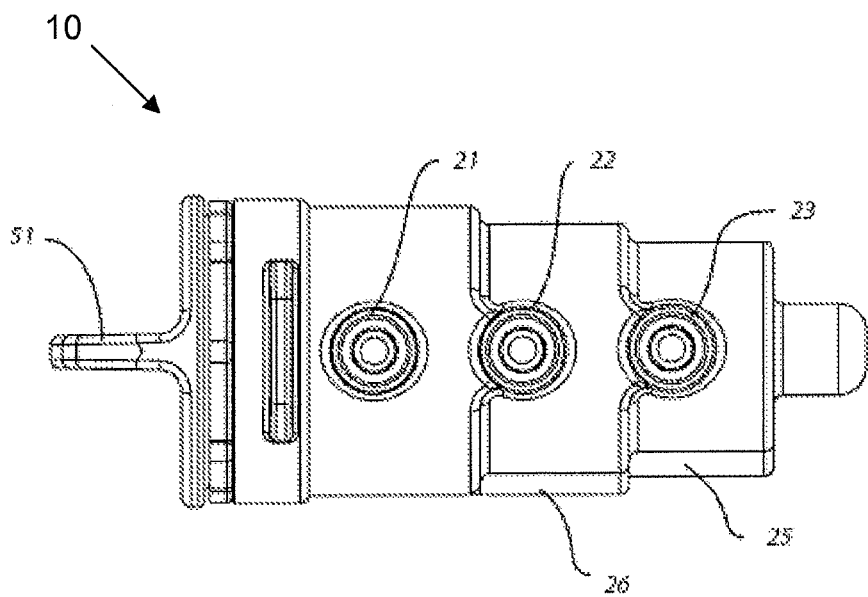

Referring to FIGS. 1A and 1B, a flow selector 10 combines fluid (e.g., a medical fluid such as a drug) arriving from multiple input ports 21, 22, 23 into a single output port 24. The flow rate of fluid exiting from output port 24 is controlled by the internal configuration of flow selector 10, which can be set by turning a control knob 51 at one end of the flow selector.

Figure 2:
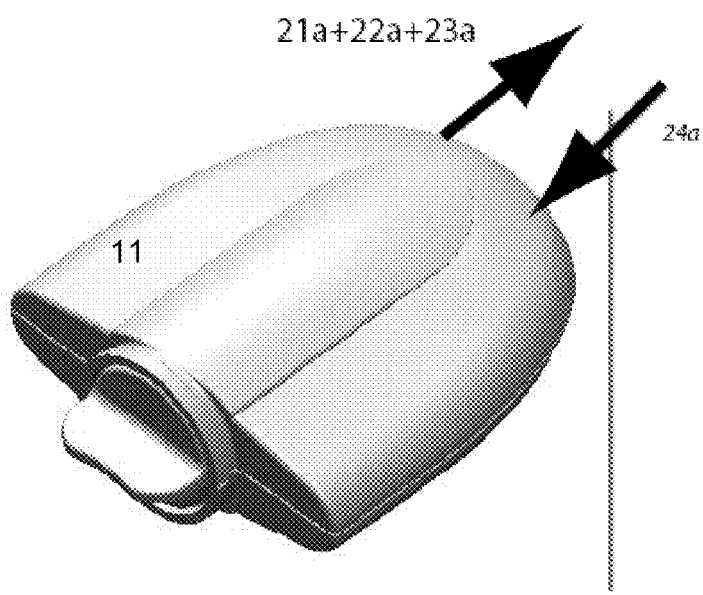
FIG. 2 is a view of a case for a flow selector.

The input ports 21, 22, 23 are coupled to fluid sources 21a, 22a, 23a, respectively. The fluid sources may be, e.g., tubes each with a different flow restrictor, such as different lumen tubes or glass capillaries with varying orifice sizes. Input ports 21, 22, 23 and output port 24 can be positioned at any position around the flow selector; the positions of the ports are not limited to the configuration shown in the figures. Referring to FIG. 2, the components of flow selector 10 are enclosed in a case 11 that provides a compact, user-friendly design.

Figure 3A:
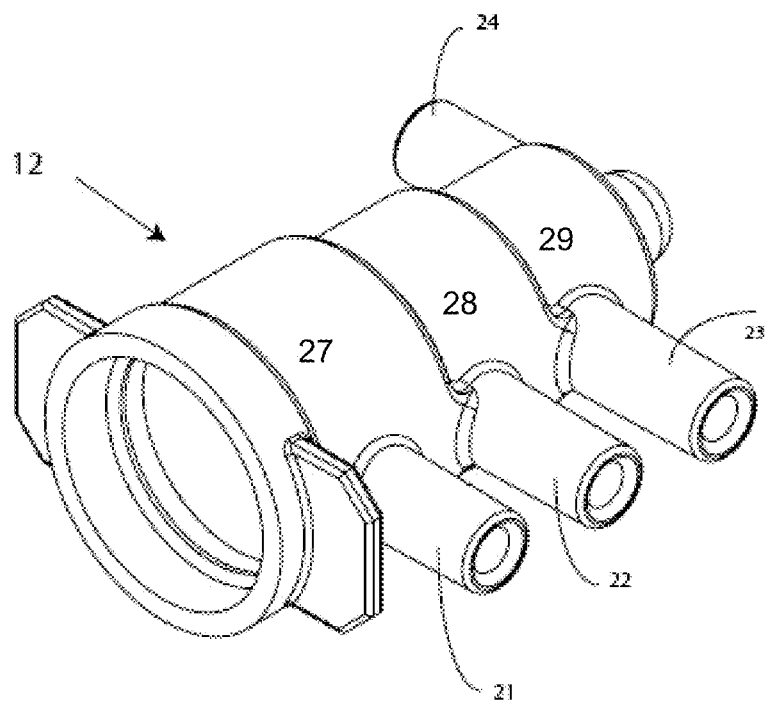
FIG. 3A is a schematic diagram of the barrel of a flow selector.
Figure 3B:
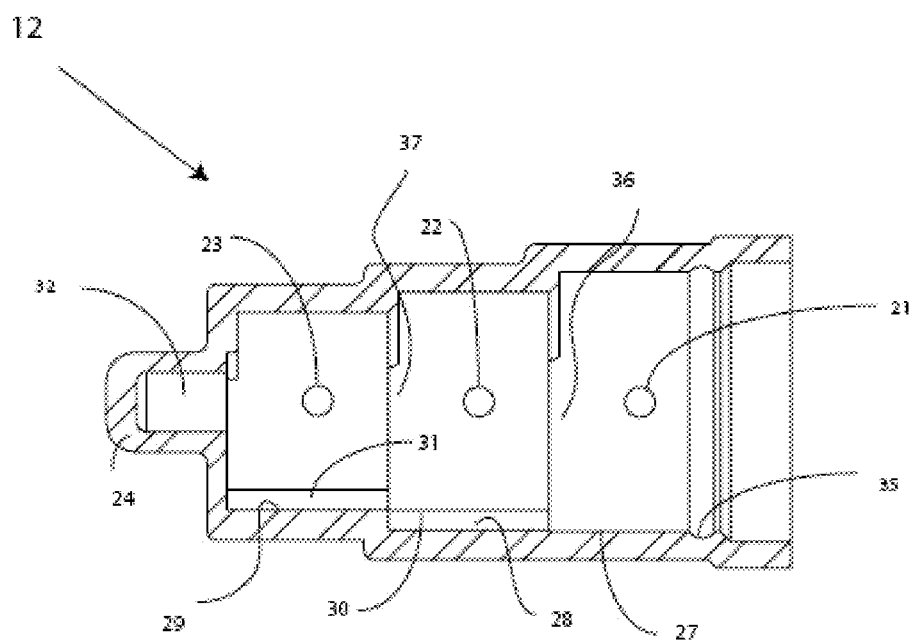
FIG. 3B is a cross-sectional side view of the barrel of FIG. 3A.
Figure 3C:
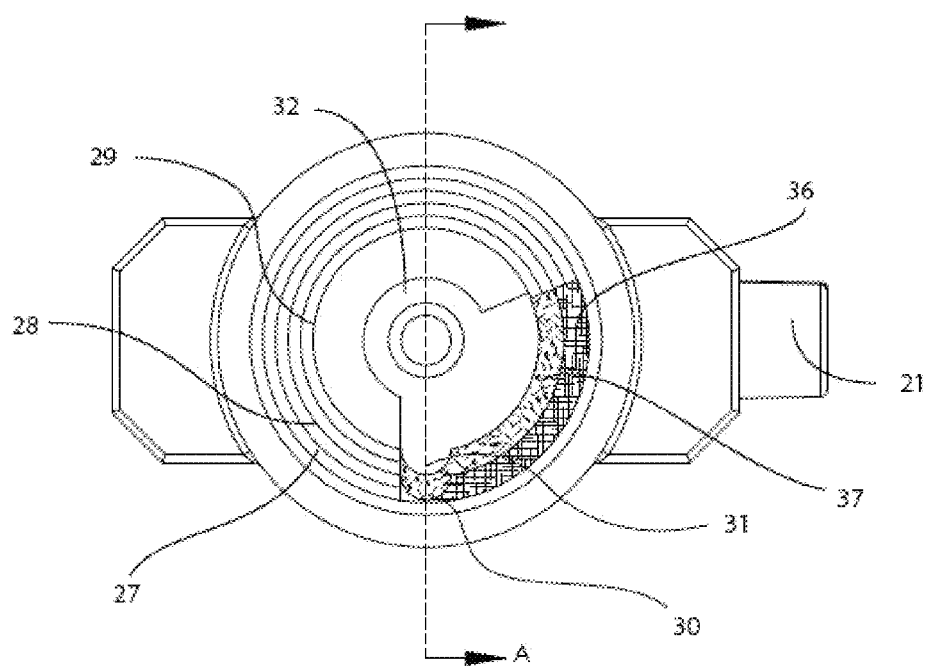
FIG. 3C is a longitudinal cross-sectional view of the barrel of FIG. 3A.

Referring to FIGS. 3A-3B, flow selector 10 includes a hollow barrel 12 formed of three stepped sections 27, 28, 29. Each stepped section 27, 28, 29 connects to one of the input ports 21, 22, 23, respectively. Referring also to FIG. 3C, grooves 36, 37 corresponding to stepped sections 27, 28, respectively, are formed around about one-quarter of the circumference of barrel 12. The remaining three-quarters of the circumference of the barrel are in substantial interference contact with the outside edge of an axle disposed within the barrel (axle 40 in FIG. 4, discussed below) in order to prevent fluid leakage. Grooves 36 and 37 are in perpetual fluid communication with drain cavities 30, 31, respectively, formed in stepped barrel sections 28 and 29.

Figure 4:
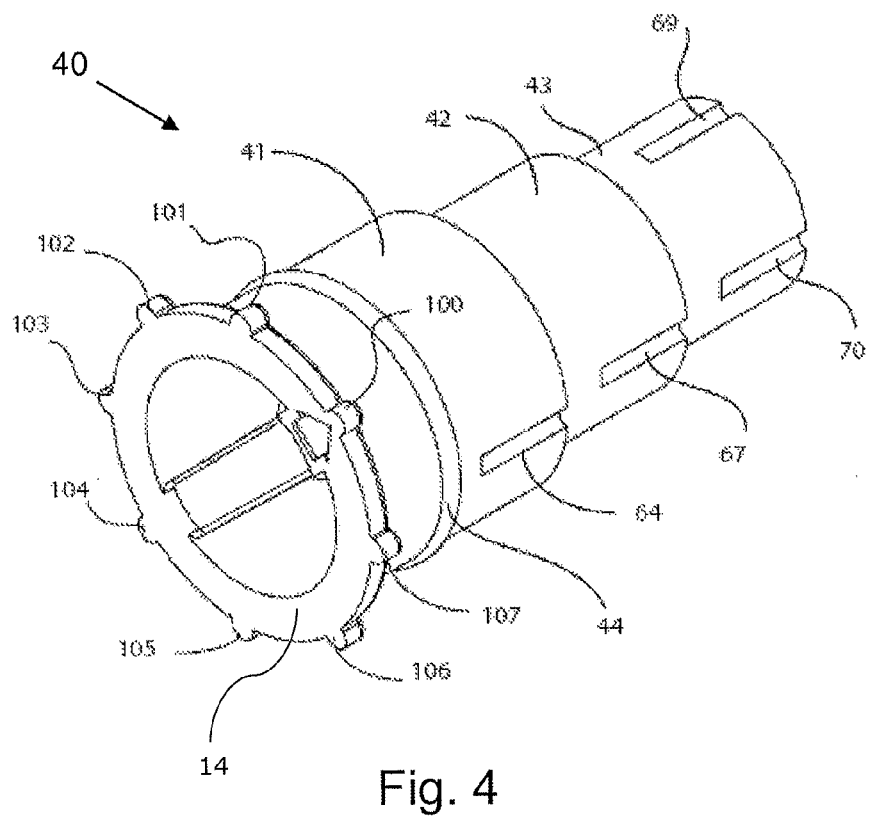
FIG. 4 is a schematic diagram of the axle of a flow selector.

Referring also to FIG. 4, a stepped axle 40 is disposed within hollow barrel 12. Stepped axle sections 41, 42, 43 nest within stepped barrel sections 27, 28, 29, respectively. To ensure leak-proof contact between axle 40 and barrel 12, a stabilizer ring 44 on axle 40 fits snugly within an annular groove 35 (see FIG. 3B) on the interior surface of barrel 12. The axle and barrel are both formed of materials that minimize leakage and facilitate rotation of the axle with minimal binding. The barrel is generally constructed from hard plastics such as Acrylonitrile Butadiene Styrene (ABS) or polycarbonate, while the axle is of material with lubricating characteristics on its surface like high-density polyethylene (HDPE) or polyethylene (PE).

Longitudinal drain channels are formed in each stepped axle section 41, 42, 43. For instance, stepped axle section 41 includes drain channels 61, 62, 63, and 64, each channel located at a different radial position around the circumference of the axle. Stepped axle section 42 includes drain channels 65, 66, 67, and 68; and stepped axle section 43 includes drain channels 69, 70, 71, and 72 (see also FIGS. 6A-6D). As discussed in greater detail below, axle 40 is rotatable within barrel 12 such that one or more of the drain channels can be aligned with a corresponding input port, allowing fluid to flow from the input port into the drain channel.

Figure 5:
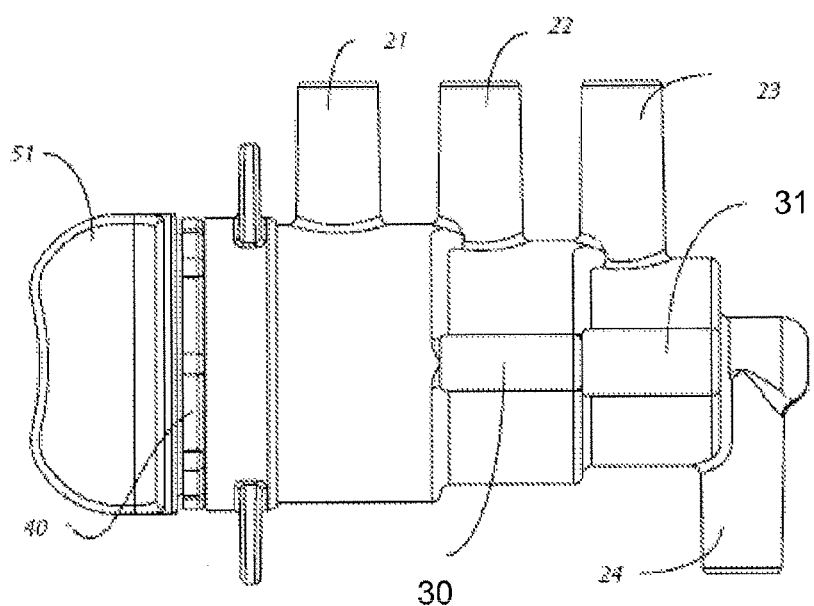
FIG. 5 is a cross-sectional top view of a flow selector.

Referring also to FIG. 5, on barrel 12, drain cavities 30, 31 are formed in stepped barrel sections 28 and 29, respectively. Fluid received into the drain channels flows between the interior surface of barrel 12 and the exterior surface of axle 40 via drain cavities 30, 31, to arrive at output port 24.

On one end of axle 40, a flow selector wheel 14 has position indicators 100, 101, 102, 103, 104, 105, 106, 107 disposed around its circumference. Each position indicator is aligned with a set of drain channels and corresponds to a different and unique flow rate of fluid through flow selector 10, as discussed in greater detail below. Using knob 51 to rotate axle 40, an operator can select the internal configuration of flow selector 10 that corresponds to a desired flow rate. In some embodiments, knob 51 is removable such that once a desired flow rate is selected, further rotation of axle 40 (and thus further adjustment of the flow rate) is disabled.

Referring to FIGS. 6A-6D, axle 40 is shown from various perspectives to demonstrate the alignment between each position indicator on flow selector wheel 14 and the corresponding set of drain channels. When a given position indicator is selected using knob 51, the corresponding set of drain channels is aligned with the lateral axis of input ports 21, 22, 23, enabling each drain channel in the selected set to receive fluid from the corresponding input port.

Figure 6A:
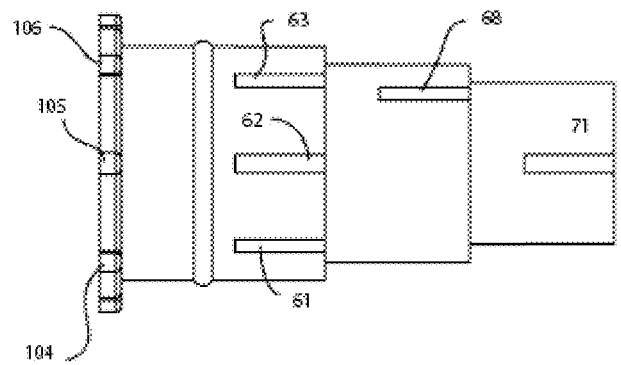
FIGS. 6A-6D are schematic diagrams of flow paths through a flow selector.
Figure 6B:
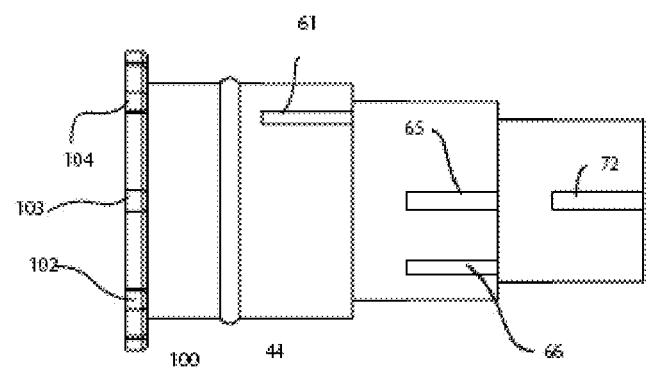

For instance, referring to FIG. 6A, position indicator 104 corresponds to a flow path involving only drain channel 61, which receives fluid from input port 21. Fluid in input ports 22 and 23 is not allowed to flow through flow selector 10 when position indicator 104 is selected. Position indicator 105 corresponds to a flow path involving drain channels 62 and 71, which are in communication with input ports 21 and 23, respectively. That is, by selecting position indicator 105, the fluid flow rate through flow selector 10 would be equal to the combined fluid flow rate through input ports 21 and 23. Position indicator 106 corresponds to a flow path involving drain channels 63 and 68, which are in communication with input ports 21 and 22, respectively. Referring now to FIG. 6B, position indicator 102 enables a flow path involving only drain channel 66, while position indicator 103 enables a flow path involving drain channels 65 and 72.

Figure 6C:
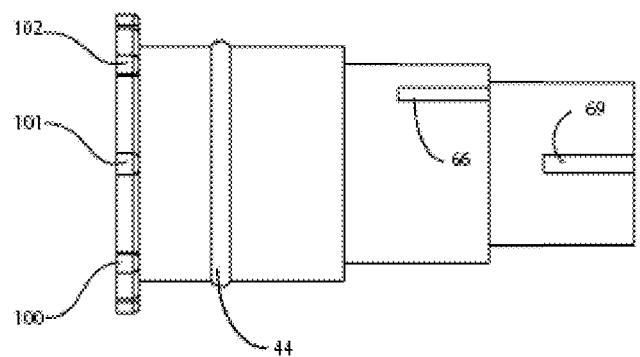
Figure 6D:
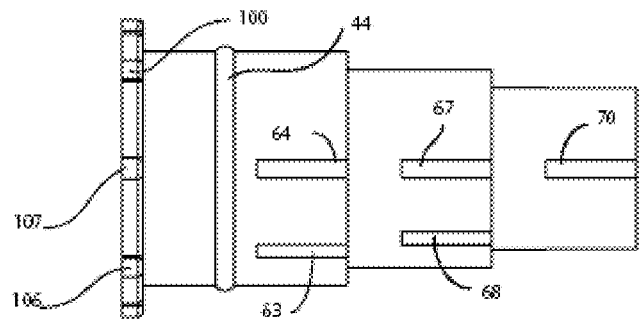

FIG. 6C shows that position indicator 101 enables a flow path involving only drain channel 69. Position indicator 100 does not correspond to any drain channel; thus, selecting position indicator 100 effectively turns off the flow of fluid through flow selector 10. In FIG. 6D, it can be seen that position indicator 107 corresponds to a flow path involving drain channels 64, 67, and 70, which are in communication with all three input ports 21, 22, and 23, respectively. That is, position indicator 107 corresponds to a maximum flow rate through flow selector 10.

Figure 7A:
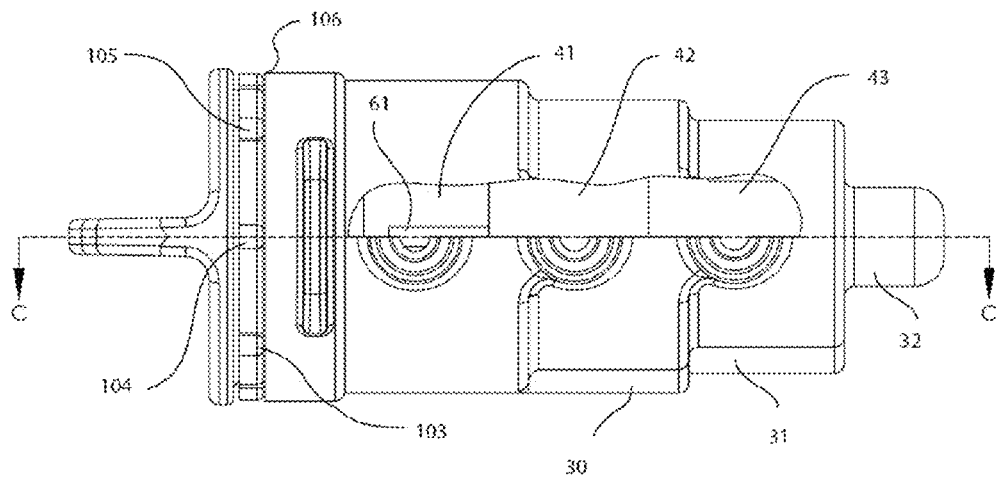
FIGS. 7A and 7B are schematic diagrams of an exemplary flow path involving one input port.
Figure 7B:
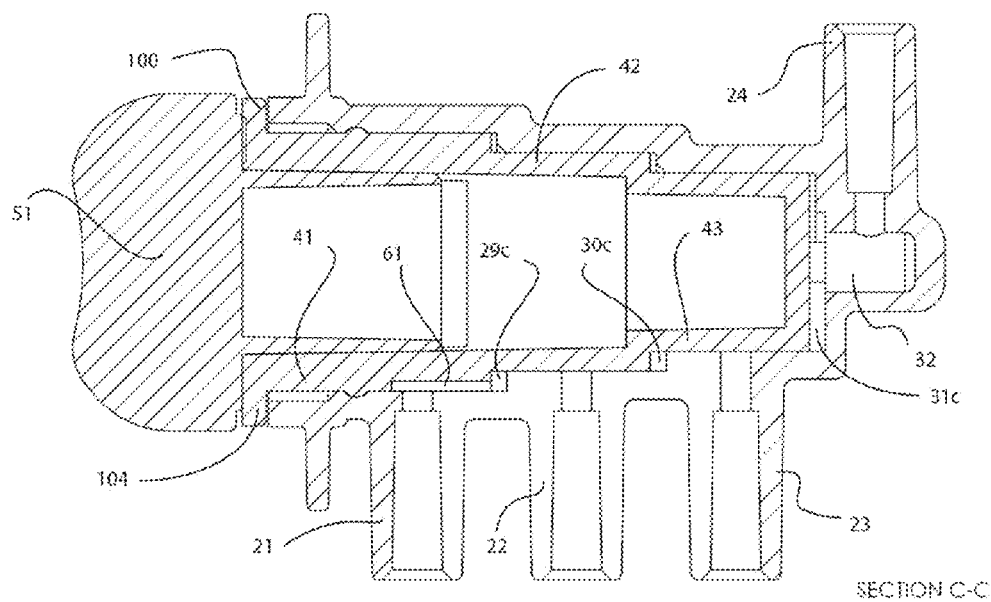

Referring to FIG. 7B, to facilitate fluid flow along flow selector 10 toward output port 24, stepped barrel sections 27, 28, 29 precisely correspond to stepped axle sections 41, 42, 43. However, at each transition between steps, a small gap form by the groove along the circumference of the barrel cavity and the edge of the axle is present through which fluid can flow. For instance, a first axle step gap 29$c$ located at the transition between the largest stepped sections (stepped barrel section 27 and stepped axle section 41) and the medium-sized stepped sections (stepped barrel section 28 and stepped axle section 42) allows fluid to exit the drain channel on stepped axle section 41 and flow towards output port 24 via cavity 30. The gap 29$c$ is formed by the groove 36 and the stepped surface 41 of axle. A second axle step gap 30$c$ is located at the transition between the medium-sized stepped sections (stepped barrel section 28 and stepped axle section 42) and the smallest stepped sections (stepped barrel section 29 and stepped axle section 42) and allows fluid to exit the drain channel on stepped axle section 42 via cavity 31. The gap 30$c$ is formed by the groove 37 and the stepped surface 42 of the axle. A third axle step gap 31$c$ is located past stepped sections 29 and 43 and allows fluid to exit the drain channel on stepped axle section 43 and flow into output port 24 via cavity 32.

Referring now to FIGS. 7A and 7B, to illustrate the fluid flow path through flow selector 10, an exemplary flow path corresponding to position indicator 104 is shown. As shown in FIG. 6A, position indicator 104 allows fluid flow only from input port 21; no drain channel accepts fluid from input ports 22 or 23. In this configuration, fluid arriving via input port 21 flows into drain channel 61 and into first axle step gap 29$c$. From first axle step gap 29$c$, the fluid flows into cavity 30, via second axle step gap 30$c$, through cavity 31, into third axle step gap 31$c$, and out of flow selector 10 via an output cavity 32 in output port 24. Supposing input port 21 is connected to a tube with a 4 mL/hour flow rate, than output port 24 would deliver fluid at a flow rate of 4 mL/hour.

Figure 8A:
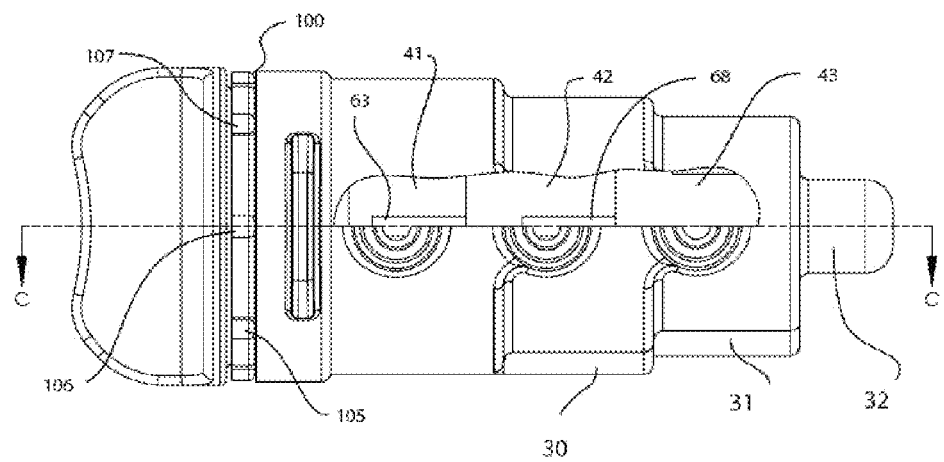
FIGS. 8A and 8B are schematic diagrams of an exemplary flow path involving two input ports.
Figure 8B:
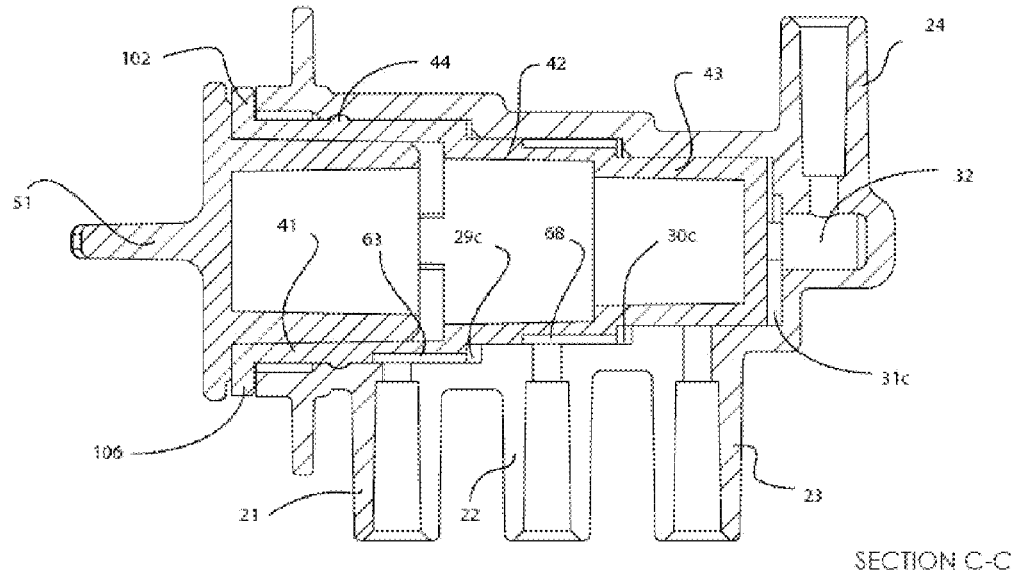

Referring to FIGS. 8A and 8B, another exemplary flow path corresponding to position indicator 106 is illustrated. In this configuration, fluid is received from both input ports 21 and 22 but not from input port 23. Fluid arriving via input port 21 flows into drain channel 63, via first axle step gap 29$c$ into cavity 30, via second axle step gap 30$c$ into cavity 31, then through third axle step gap 31$c$ and out of flow selector via output port 24. Fluid arriving via input port 22 flows into drain channel 68, via second axle step gap 30c and into cavity 31, then through third axle step gap 31c and out of the flow selector via output cavity 32 in output port 24. Supposing input port 21 is connected to a tube with a 4 mL/hour flow rate and input port 22 is connected to a tube with a 2 mL/hour flow rate, then output port 24 would deliver fluid at a flow rate of 6 mL/hour.

Figure 9A:
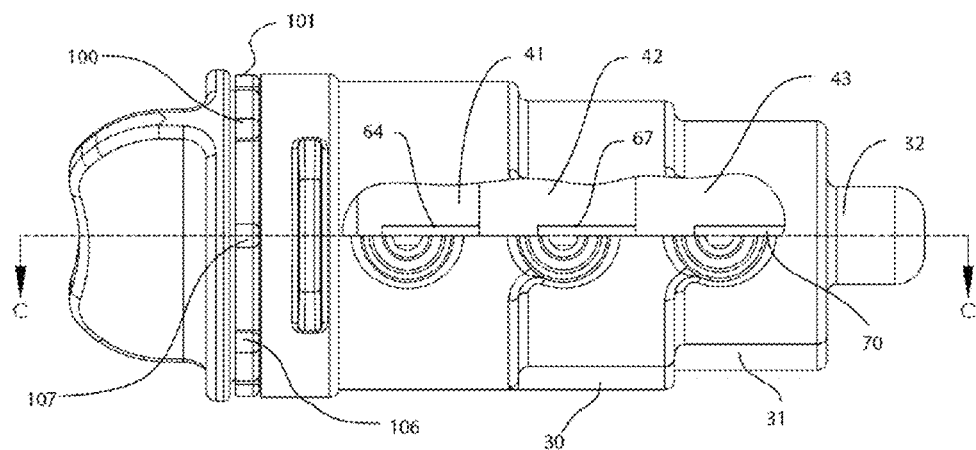
FIGS. 9A and 9B are schematic diagrams of an exemplary flow path involving three input ports.
Figure 9B:
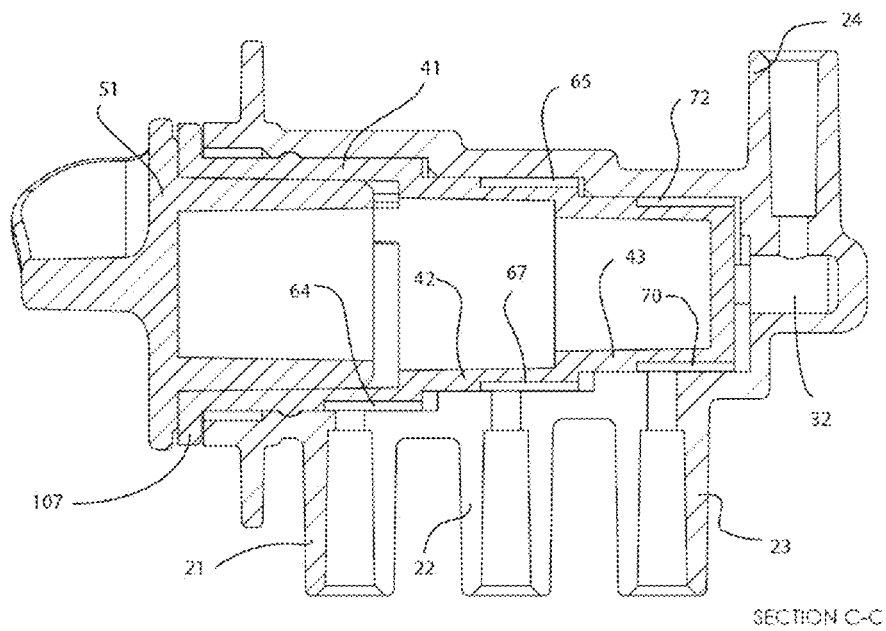

Referring to FIGS. 9A and 9B, another exemplary flow path corresponding to position indicator 107 is illustrated. In this configuration, fluid is received from all three input ports 21, 22, and 23. Fluid arriving via input port 21 flows into drain channel 64, via first axle step gap 29c into cavity 30, via second axle step gap 30c into cavity 31, then through third axle step gap 31c and out of flow selector via output port 24. Fluid arriving via input port 22 flows into drain channel 67, via second axle step gap 30c and into cavity 31, then through third axle step gap 31c and out of the flow selector via output port 24. Fluid arriving via input port 23 flows into drain channel 70, through third axle step gap 31c, and out of the flow selector via output cavity 32 in output port 24. Supposing input port 21 is connected to a tube with a 4 mL/hour flow rate, input port 22 is connected to a tube with a 2 mL/hour flow rate, and input port 23 is connected to a tube with 1 mL/hour flow rate, then output port 24 would deliver fluid at a flow rate of 7 mL/hour.

Figure 10A:
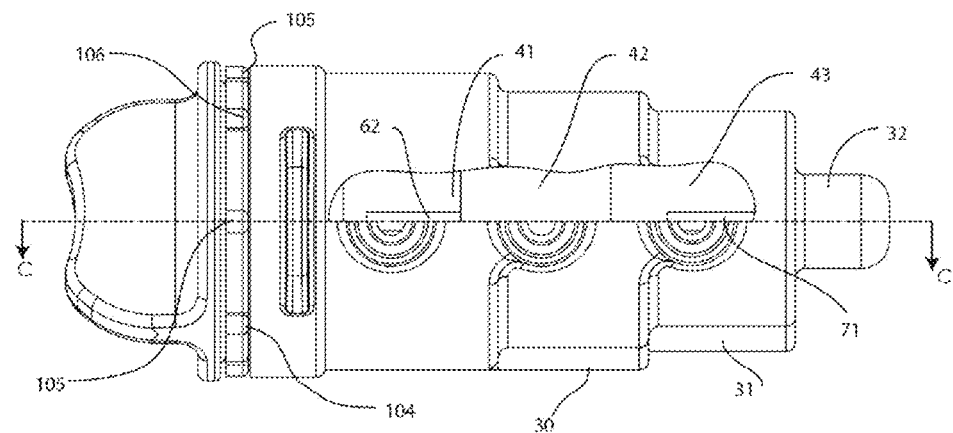
FIGS. 10A and 10B are schematic diagrams of an exemplary flow path involving two input ports.
Figure 10B:
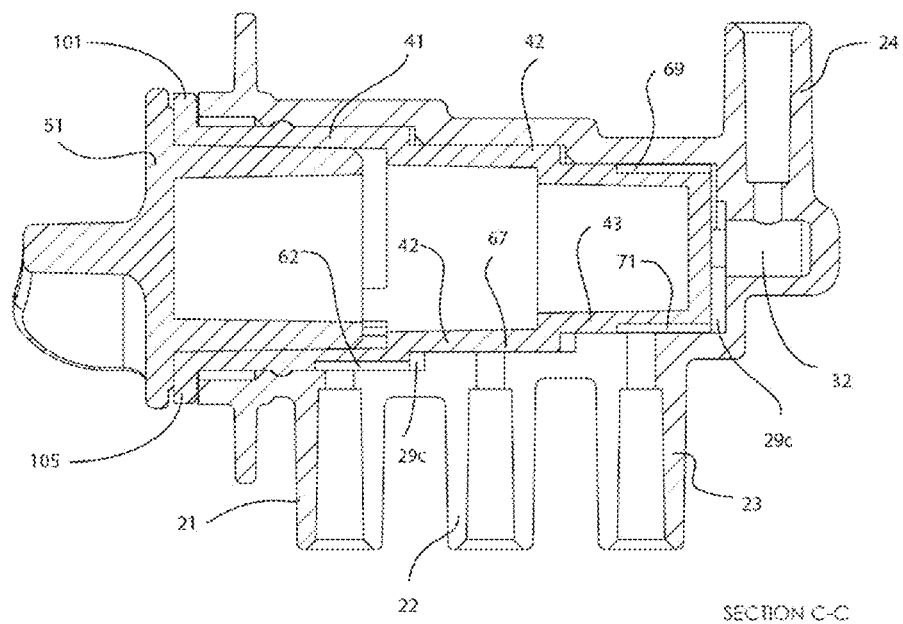

Referring to FIGS. 10A and 10B, another exemplary flow path corresponding to position indicator 105 is illustrated. In this configuration, fluid is received from input ports 21 and 23. Fluid arriving via input port 21 flows into drain channel 62, via first axle step gap 29c into cavity 30, via second axle step gap 30c into cavity 31, then through third axle step gap 31c and out of flow selector via output port 24. Fluid arriving via input port 23 flows into drain channel 71, through third axle step gap 31c, and out of the flow selector via output cavity 32 in output port 24. Supposing input port 21 is connected to a tube with a 4 mL/hour flow rate and input port 23 is connected to a tube with 1 mL/hour flow rate, then output port 24 would deliver fluid at a flow rate of 5 mL/hour.

Figure 11A:
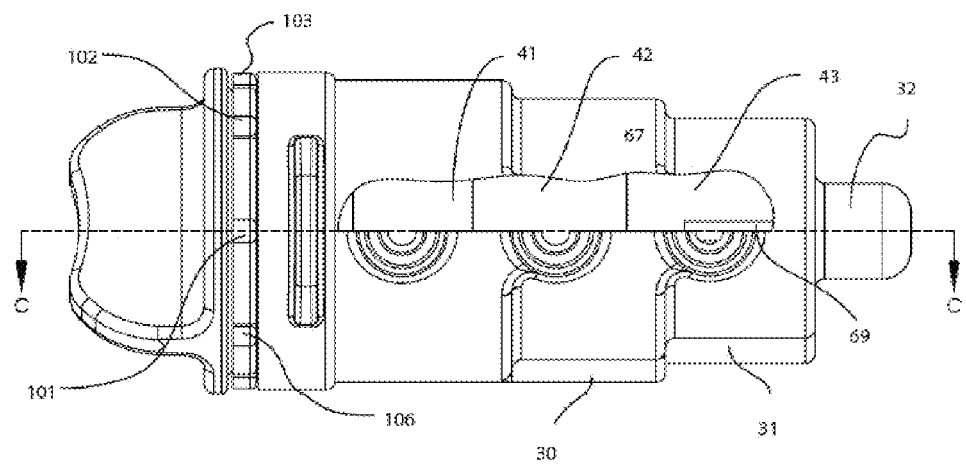
FIGS. 11A and 11B are schematic diagrams of an exemplary flow path involving one input port.
Figure 11B:
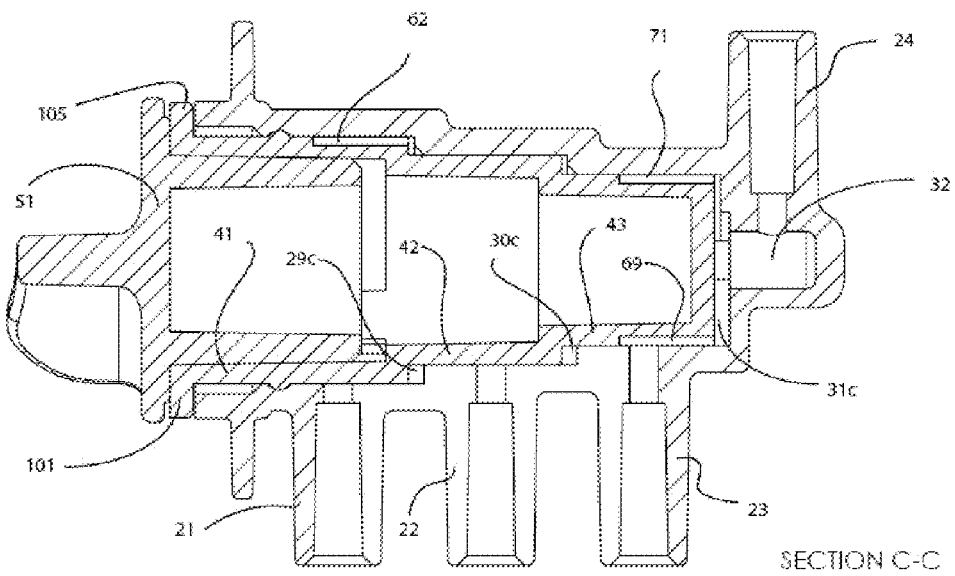

Referring to FIGS. 11A and 11B, another exemplary flow path corresponding to position indicator 101 is illustrated. In this configuration, fluid is only received from input port 23. From input port 23, the fluid flows into drain channel 69, through third axle step gap 31c, and out of the flow selector via output cavity 32 in output port 24. Supposing input port input port 23 is connected to a tube with 1 mL/hour flow rate, then output port 24 would deliver fluid at a flow rate of 1 mL/hour.

Figure 12A:
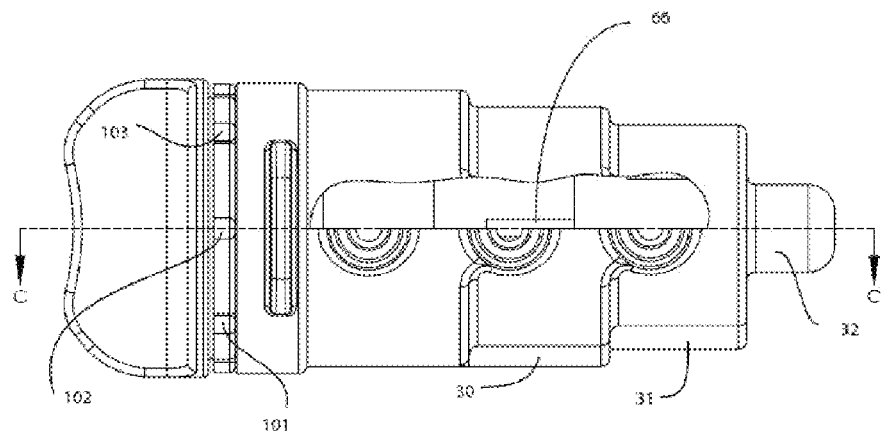
FIGS. 12A and 12B are schematic diagrams of an exemplary flow path involving one input port.
Figure 12B:
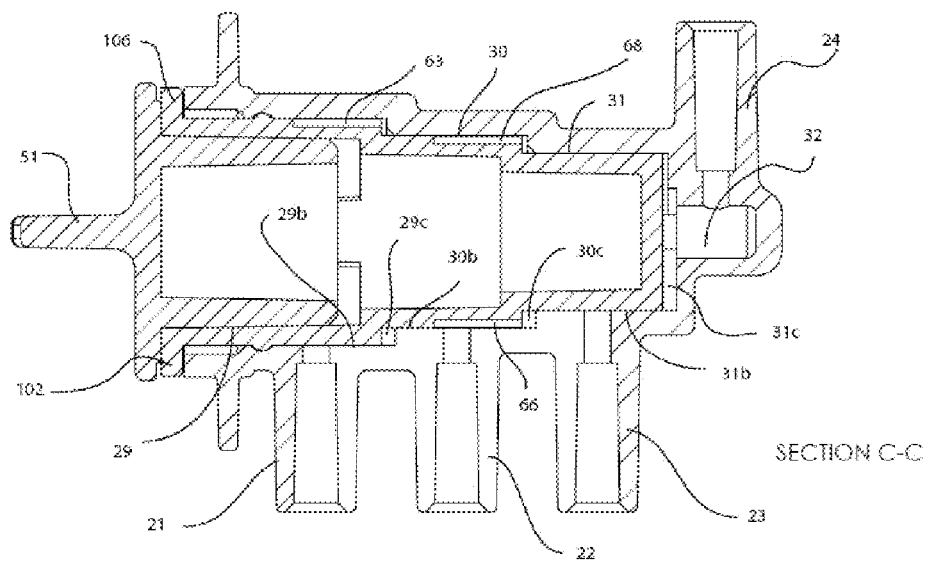

Referring to FIGS. 12A and 12B, another exemplary flow path corresponding to position indicator 102 is illustrated. In this configuration, fluid is only received from input port 22. From input port 22, the fluid flows into drain channel 66, via second axle step gap 30c and into cavity 31, then through third axle step gap 31c and out of the flow selector via output cavity 32 in output port 24. Supposing input port 22 is connected to a tube with a 2 mL/hour flow rate, then output port 24 would deliver fluid at a flow rate of 2 mL/hour.

Figure 13A:
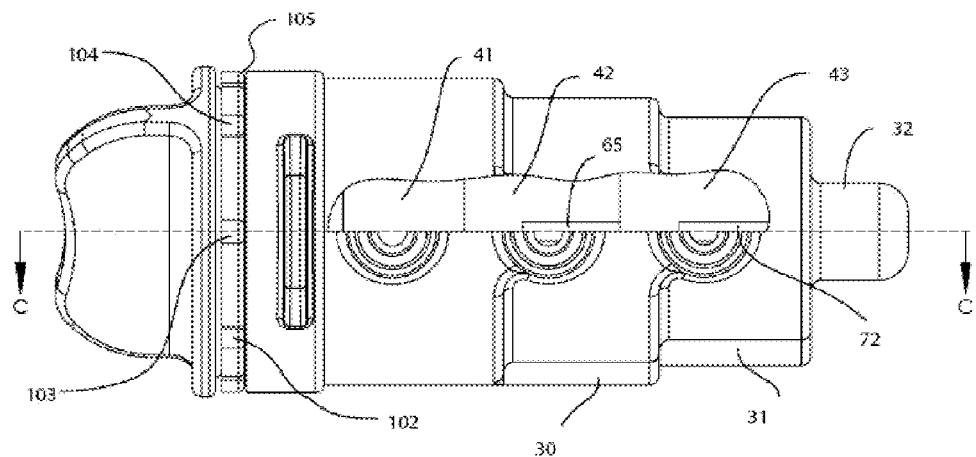
FIGS. 13A and 13B are schematic diagrams of an exemplary flow path involving two input ports.
Figure 13B:
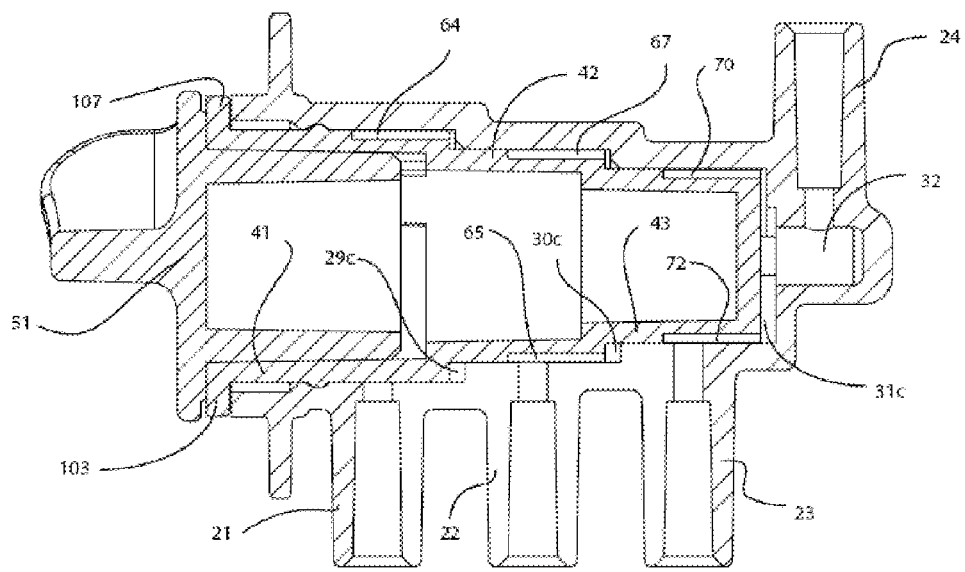

Referring to FIGS. 13A and 13B, another exemplary flow path corresponding to position indicator 103 is illustrated. In this configuration, fluid is received from input ports 22 and 23. Fluid arriving via input port 22 flows into drain channel 65, via second axle step gap 30c and into cavity 31, then through third axle step gap 31c and out of the flow selector via output port 24. Fluid arriving via input port 23 flows into drain channel 72, through third axle step gap 31c, and out of the flow selector via output cavity 32 in output port 24. Supposing input port 22 is connected to a tube with a 2 mL/hour flow rate and input port 23 is connected to a tube with 1 mL/hour flow rate, then output port 24 would deliver fluid at a flow rate of 3 mL/hour.

Figure 14A:
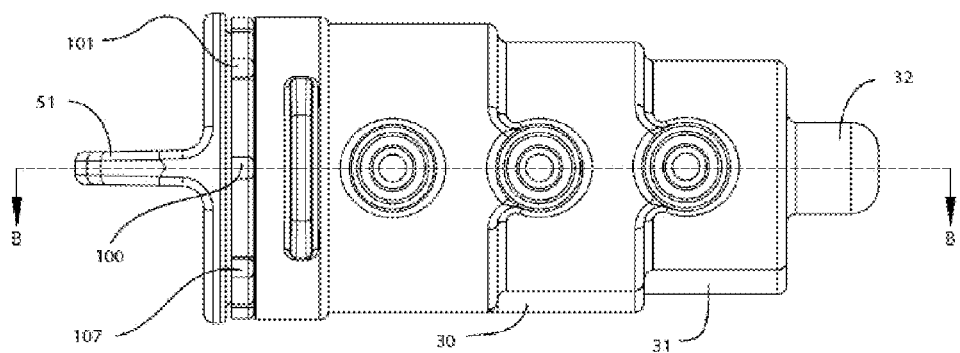
FIGS. 14A and 14B are schematic diagrams of an exemplary flow path involving no input ports.
Figure 14B:
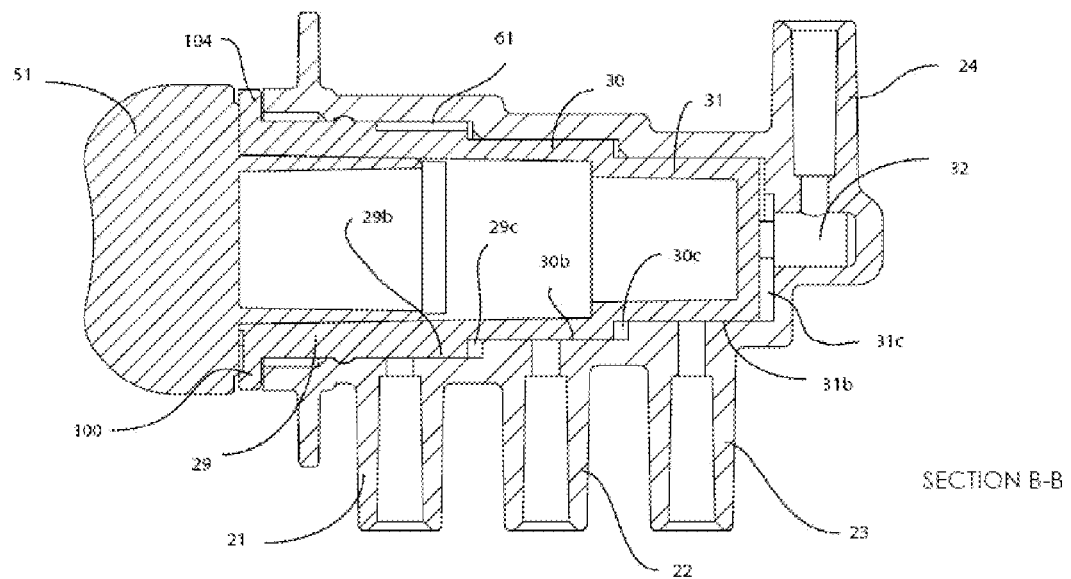

Referring to FIGS. 14A and 14B, when position indicator 100 is selected, none of the input ports 21, 22, or 23 is aligned with a drain channel and there is no fluid flow through the flow selector.

In the embodiment described above, axle 40 includes eight position indicators corresponding to eight unique flow paths. However, the number of position indicators is not necessarily limited to eight, but varies depending on the number of input ports. In general, the number of combinations of input ports (and hence the number of unique flow paths) is $2^N-1$, where N is the number of unique input ports.

Referring again to FIG. 1A, in some embodiments, flow selector 10 may be configured in a reverse fashion such that port 24 acts as an input port that receives fluid from a fluid source 24a and ports 21, 22, and 23 act as three separate output ports. In this case, the flow selector selects some or all of the ports 21, 22, 23 through which to output fluid.

It is to be understood that the foregoing description is intended to illustrate and not to limit the scope of the invention, which is defined by the scope of the appended claims. Other embodiments are within the scope of the following claims.

What is claimed is:

1. An apparatus for selecting a flow rate of a fluid, the apparatus comprising:
   a barrel including an output port, a plurality of input ports, and a plurality of drain cavities formed longitudinally along an inner surface of the barrel; and
   an axle disposed substantially concentrically within the barrel, wherein a plurality of drain channels are formed on an outer surface of the axle, each of the plurality of drain channels having a depth less than a thickness of a wall of the axle and configured to align with at least one of the plurality of drain cavities,
   wherein the axle is rotatable within the barrel to provide one of a plurality of flow paths between one of the plurality of input ports and the output port, each of the plurality of flow paths at least partially defined by at least one of the plurality of drain channels aligning with at least one of the plurality of drain cavities.

2. The apparatus of claim 1, wherein the axle is formed of a plurality of axle segments, each axle segment having a different radius.

3. The apparatus of claim 2, wherein the barrel is formed of a plurality of barrel segments, each barrel segment having a different radius, each barrel segment corresponding to one of the plurality of axle segments.

4. The apparatus of claim 3, wherein an outer surface of each of the plurality of axle segments is in contact with an inner surface of the corresponding one of the plurality barrel segments.

5. The apparatus of claim 3, wherein a drain cavity is formed in the inner surface of at least one of the plurality of barrel segments, at least one of the plurality of flow paths further defined by the drain cavity.

6. The apparatus of claim 3, wherein each barrel segment corresponds to one of the plurality of input ports.

7. The apparatus of claim 2, wherein the plurality of drain channels are formed in an outer surface of the plurality of axle segments.

8. The apparatus of claim 7, wherein each flow path is defined by no more than one drain channel on each of the plurality of axle segments.

9. The apparatus of claim 1, wherein the flow rate of the fluid is selected by rotating the axle to a position such that at least one of the plurality of drain channels is aligned with at least one of the plurality of input ports.

10. The apparatus of claim 9, wherein the flow rate of the fluid comprises the sum of the flow rates of the fluid through the at least one of the plurality of input ports aligned with the at least one of the plurality of drain channels.

11. The apparatus of claim 1, further comprising a control knob configured to rotate the axle.

12. The apparatus of claim 11, wherein the control knob includes a plurality of position identifiers, each position identifier corresponding to one of the plurality of flow paths.

13. The apparatus of claim 11, wherein the control knob is removable, and wherein rotation of the axle is prohibited after removal of the control knob.

14. The apparatus of claim 1, wherein the number of flow paths is $2^N-1$, where N is the number of input ports.

15. The apparatus of claim 1, wherein at least some of the plurality of flow paths correspond to different flow rates.

16. The apparatus of claim 1, wherein the barrel includes a groove configured to receive a stabilizer ring formed on the outer surface of the axle.

17. The apparatus of claim 1, wherein the fluid comprises a medical fluid.

18. An apparatus for selecting a flow rate of a fluid, the apparatus comprising:

a barrel formed of a plurality of barrel segments, each barrel segment having a different radius, wherein the barrel has an output port and a plurality of input ports; and an axle formed of a plurality of axle segments, each axle segment having a different radius, wherein each barrel segment corresponds to one of the plurality of axle segments, wherein the axle is disposed substantially concentrically within the barrel, wherein a plurality of drain channels are formed in an outer surface of the axle, each of the plurality of drain channels having a depth less than a thickness of a wall of the axle, wherein the axle is rotatable within the barrel to provide one of a plurality of flow paths between one of the plurality of input ports and the output port, each of the plurality of flow paths at least partially defined by at least one of the plurality of drain channels, wherein at least one gap is present between the axle and the barrel, each gap located at a boundary between one of the plurality of barrel segments and an adjacent one of the plurality of barrel segments.

19. The apparatus of claim 18, wherein at least one of the plurality of flow paths is further defined by the at least one gap.

* * * * *